United States Patent
Smith et al.

(10) Patent No.: US 6,194,000 B1
(45) Date of Patent: Feb. 27, 2001

(54) ANALGESIC IMMEDIATE AND CONTROLLED RELEASE PHARMACEUTICAL COMPOSITION

(75) Inventors: Ian Keith Smith, Blair Athol; Grant Wayne Heinicke, Fairview Park, both of (AU)

(73) Assignee: F.H. Faulding & Co., Limited, Underdale (AU)

( * ) Notice: Subject to any disclaimer, the term of this patent is extended or adjusted under 35 U.S.C. 154(b) by 0 days.

(21) Appl. No.: 09/062,060

(22) Filed: Apr. 17, 1998

Related U.S. Application Data

(63) Continuation of application No. PCT/AU96/00658, filed on Oct. 8, 1996.

(30) Foreign Application Priority Data

Oct. 19, 1995 (AU) .......................................... 6057

(51) Int. Cl.⁷ ................ A61K 9/14; A61K 9/20; A61K 9/22; A61K 9/24; A61K 9/54
(52) U.S. Cl. .......... 424/458; 424/422; 424/423; 424/436; 424/449; 424/451; 424/455; 424/457; 424/464; 424/465; 424/468; 424/472; 424/473; 424/489; 424/490; 424/483; 424/484; 424/485; 424/486; 424/487; 424/488; 514/770; 514/772.2; 514/772.3; 514/773; 514/777; 514/781; 514/782; 514/783; 514/784; 514/785; 514/786; 514/787
(58) Field of Search .................... 424/464, 468, 424/490, 422, 423, 436, 449, 451, 457, 458, 483, 473, 455, 489, 472, 465, 484, 485, 486, 487, 488

(56) References Cited

U.S. PATENT DOCUMENTS

| | | | |
|---|---|---|---|
| 4,859,461 | * 8/1989 | Chow et al. | 424/79 |
| 4,859,462 | * 8/1989 | Chow et al. | 424/79 |
| 5,084,278 | * 1/1992 | Mehta | 424/441 |
| 5,352,683 | 10/1994 | Mayer et al. . | |
| 5,502,058 | 3/1996 | Mayer . | |
| 5,834,479 | 11/1998 | Mayer et al. . | |
| 5,840,731 | 11/1998 | Mayer et al. . | |

OTHER PUBLICATIONS

Chapman, C.R. et al., "Pain Measurement: an Overview", *Pain*, 22 (1985) pp. 1–31.

Hawthorn, Jan et al., "Management of Cancer Pain: International Training for Cancer Nurses", developed by Glaxo Wellcome in collaboration with The International Society of Nurses in Cancer Care, 1996, 6 pp.

* cited by examiner

*Primary Examiner*—James M. Spear
(74) *Attorney, Agent, or Firm*—Cohen, Pontani, Lieberman & Pavane

(57) ABSTRACT

Disclosed is a method for the therapeutic treatment of pain related to wind up in a human or animal. The method of the invention is practiced by administering to the subject an effective amount of an analgesic pharmaceutical composition which includes a NMDA receptor antagonist in an immediate release form combined with an NMDA receptor antagonist in a sustained release form. The immediate release form and sustained release forn are present in sufficient amounts to diminsh or abolish wind up.

48 Claims, 2 Drawing Sheets

ANALGESIC IMMEDIATE AND CONTROLLED RELEASE PHARMACEUTICAL COMPOSITION

This application is a continuation of PCT/AU96/00658 filed Oct. 18, 1996.

The present invention relates to pharmaceutical compositions and is particularly concerned with pharmaceutical compositions containing N-methyl-D-aspartate (NMDA) receptor antagonists and their use in the treatment of pain.

BACKGROUND OF THE INVENTION

The amino acid glutamate is an excitatory neurotransmitter that is an agonist at many post-synaptic terminals of the central nervous system. The glutamate receptor complex is termed the NMDA receptor and is a potential target for therapeutic drugs. This receptor incorporates an ion channel complex which is novel because it is gated by both dual ligand binding (glutamate and glycine) and membrane voltage. Because of the novel requirements for activation, it is believed that the NMDA receptor complex plays only a minor role in routine synaptic transmission. However, the receptor complex may be activated following repeated afferent stimuli as occurs during trauma such as surgery. Repeated stimuli cause a temporal summation of C-fibre-mediated responses of dorsal horn nociceptive neurones; this phenomenon, increased output to a constant input, is known as wind-up.

Studies indicate that activation of the NMDA receptor complex in the spinal dorsal horn leads to increased spontaneous neural discharge, expanded receptive fields and exaggerated responses to afferent input. These neural mechanisms may be expressed physically as hyperalgesia (increased pain sensation) and allodynia (pain arising from a stimulus that is not normally painful).

Opioids, through their ability to inhibit release of primary afferent neurotransmitters or to inhibit interneurons early in nociceptive pathways, initially reduce or block C-fibre inputs to the deeper dorsal horn nociceptive neurones. However, as the peripheral stimulation continues, wind-up breaks through the input inhibition and the neurones start to respond. Thus at moderate doses, opioids delay the onset of wind-up without inhibiting the process itself.

By contrast, NMDA receptor antagonists have no effect on the initial inputs to the cells but diminish or abolish wind-up and convert the potentiated response to a normal response.

We have found that a particularly effective composition for the administration of an NMDA receptor antagonist to diminish or abolish wind up is one providing both immediate release of an NMDA receptor antagonist and controlled or sustained release of an NMDA receptor antagonist.

NMDA antagonist receptors have also been indicated to be effective in the treatment of Huntington's disease, amyotrophic lateral sclerosis (ALS), AIDS-related dementia, Alzheimer's disease, schizophrenia, motoneurone diseases and CNS and brain injuries resulting from a number of causes including stroke, trauma and neurosurgery.

THE INVENTION

In accordance with one aspect of the present invention there is provided a pharmaceutical composition for the administration of an NMDA receptor antagonist to a human or animal subject, the composition including an NMDA receptor antagonist in an immediate release form in association with an NMDA receptor antagonist in a controlled release form.

The same NMDA receptor antagonist may be used in both the immediate and controlled release forms or they may be different NMDA receptor antagonists.

The composition of the invention is suitable for the treatment of chronic or acute pain, for example to be administered pre-operatively.

Accordingly, the present invention further provides a method for the therapeutic or prophylactic treatment of pain in a human or animal subject, the method including administering to the subject, a composition in accordance with the present invention. The method of the invention may be used to treat chronic or acute pain.

The composition of the invention may be used in the pre-emptive treatment of pain. The various features of novelty which characterize the invention are pointed out with particularity in the claims next to and form a part of the specification. For a better understanding of the invention, its operative advantages and specific objects obtained by its use, reference should be had to the accompanying drawings and descriptive matter in which there is illustrated and described in the preferred embodiment of the invention.

Preferably the NMDA receptor antagonist may be selected from a morphinan such as dextromethorphan and dextrorphan, ketamine, amantadine, memantine, eliprodil, ifenprodil, dizocilpine, remacemide, iamotrigine, riluzole, aptiganel, phencyclidine, flupirtine, celfotel, felbamate, spermine, spermidine, levemopamil, a pharmaceutically acceptable salt or ester thereof, or a metabolic precursor of any of the foregoing.

The formulation may include sufficient NMDA receptor antagonist to provide from about 1–5000 mg/day, typically 1–1000 mg/day and preferably about 100–800 mg/day of the active ingredient. The composition includes an NMDA receptor antagonist in an immediate release form in association with a NMDA receptor antagonist in a controlled release form. The composition may include an amount of NMDA receptor antagonist in the immediate release form of approximately 5% to 90% of the total NMDA receptor antagonist, preferably 10% to 60%. An immediate release NMDA receptor antagonist content of about 15% to 50% is particularly preferred. The controlled release form of the NMDA receptor antagonist may constitute the remainder of the active ingredients.

The composition of the invention may be in a form suitable for oral or rectal administration or for administration by transdermal, intravenous, intramuscular, subcutaneous, intrathecal, epidural or intracerebroventricular means.

The composition of the invention may or may not be in a single dosage form. Preferably the composition is in a single dose form.

The composition may be formulated as an oral dosage form such as a tablet, capsule, a liquid, powder, granule or suspension, an injectable solution, a suppository, implant or transdermal patch.

Preferably the NMDA receptor antagonist is dextromethorphan (DM) or a pharmaceutically acceptable salt thereof. Preferably the dextromethorphan is in the form of dextromethorphan hydrobromide.

The oral form of the pharmaceutical compositions of the invention may be selected from:

1) liquids, for example, suspensions, reconstitutable powders, elixirs, oils, solutions, or emulsions;
2) confectionery, for example, chewing gums, lozenges or candy bars;
3) powders, for example, drug powder, prilled material, coated actives or granulated materials;
4) capsules, for example, soft gelatin, hard gelatin containing, pellets, powders, tablets, granulates, liquids, or combinations of these; said capsules may or may not be coated;
5) tablets, for example, disintegrating, chewable effervescent, matrix, osmotic pumps, prepared by multi-layering, contain coated powders in tablets, tablets in tablets, pellets in tablets etc, said tablets may or may not be coated.

The oral pharmaceutical composition of the invention may be in the form of a "taste-masked" or "taste-neutral" form.

The method of manufacture, components and quantities of components used, depend on the particular pharmaceutical composition being considered.

A suitable immediate release (IR) form of the NMDA receptor antagonist may simply be particles of the antagonist or particles of the antagonist admixed with soluble components for example, sugars (eg sucrose, lactose, fructose, mannitol etc.), polymers (eg polyethylene glycol, hydroxypropyl cellulose, hydroxypropyl methyl cellulose, etc), surfactants (sodium lauryl sulphate, chremophor, tweens, spans, pluronics, and the like), insoluble components (microcrystalline cellulose, $Ca_3(PO_4)_2$, talc, fumed silica, i.e. aerosil® and the like), coating material (examples of suitable coating materials are polyethylene glycol, hydroxypropyl methyl cellulose, wax, fatty acids, etc.), dispersions in suitable material (examples are wax, polymers, pharmaceutically acceptable oils, soluble agents etc) or combinations of the above. These mixtures may be prepared by blending, mixing, dissolution and evaporation, or by using suspensions etc. These mixtures may be deposited on inert cores, wet massed and extruded, granulated, spray dried, etc. These mixtures or processed mixtures may be used in suspensions, filled into capsules, tabletted, filled into sachets, used in confectionery and so on.

The controlled release may be a sustained release or delayed/modified release.

A controlled-release dosage form as defined in US Pharmacopeia XXII includes extended release dosage forms which allow at least a twofold reduction in dosing frequency as compared to the drug presented as a conventional dosage form and delayed release dosage forms which release the drug at a time other than promptly after administration.

A core used herein the description contains the active ingredient and other carriers and excipients, fillers, stablising agents, binders, core seeds or colorants. The active component may be present in amounts of approximately 0.1 to 95% by weight based on the weight of the total core element. Preferably the active components is present in amounts of 10 to 80% by weight based on the weight of the total core element. The core may be 200 to 1700μ in diameter.

A pellet is a coated core, the coating being any suitable coating.

Preferably, the controlled release component is a sustained (or extended) release form.

A suitable sustained release (SR) form of the NMDA receptor antagonist may be a matrix tablet composition. Suitable matrix forming materials are waxes (eg. carnauba, bees wax, paraffin wax, ceresine, shellac wax, fatty acids, fatty alcohols), oils, hardened oils or fats (eg. hardened rapeseed oil, castor oil, beef tallow, palm dil, soya bean oil), polymers (eg. hydroxypropyl cellulose, polyvinylpyrrolidone, hydroxypropyl methyl cellulose, polyethylene glycol) and other excipients known to those familiar with the art. Other suitable matrix tabletting materials are microcrystalline cellulose, powdered cellulose, hydroxypropyl cellulose, ethyl cellulose, with other carriers, fillers, and excipients known to those familiar with the art. SR tablets may contain granulates, coated powders, pellets, or be multi-layered and the finished tablet may be coated or uncoated.

Suitable coating materials to prepare SR products are any pharmaceutically acceptable polymer such as ethyl cellulose, cellulose acetate butyrate, cellulose acetates, polymethacrylates containing quaternary ammonium groups or other pharmaceutically acceptable polymers, polyethylene glycol, hydroxypropyl cellulose, hydroxypropyl methyl cellulose, polyvinylpyrrolidone, polyvinyl alcohol, and monomeric materials such as sugars including lactose, sucrose, fructose and mannitol, salts including sodium chloride, potassium chloride and derivatives, organic acids including fumaric acid, succinic acid, lactic acid and tartaric acid and mixtures thereof, enteric polymers including hydroxypropyl cellulose, hydroxypropyl methyl cellulose, polyvinyl acetate phthalate, cellulose acetate phthalate, cellulose acetate trimellitate, shellac, zein, and polymethacrylates containing carboxyl groups. These polymers may be applied as solutions or latexes. Other barriers may be used such as waxes.

The coating composition may or may not be plasticised according to the properties of the coating blend such as the glass transition temperature of the main component or mixture of components or the solvent used for applying the coating compositions. Suitable plasticises can be added from 0 to 50% by weight of the coating composition and at least one may be selected from diethyl phthalate, citrate esters, polyethylene glycol, glycerol, acetylated glycerides, castor oil and the like.

Cores containing active may be coated directly to produce a SR dose, or tablets or capsules containing active may be coated.

A suitable SR form of NMDA receptor antagonist may be an osmotic pump, or combinations of the above.

These IR or SR forms may be made by prilling, spray drying, pan coating, melt granulation, granulation, wurster coating, tangential coating, top spray, tabletting, extruding, coacervation and the like.

The particle sizes of the IR and SR components in the dosage form depends on the technology used. The particle sizes component range from submicron to 500 µm for powder technologies (mixtures, spray drying, dispersions etc), 5–1700 µm for coating technologies (wurster, top spray, bottom spray, spray drying, extrusion, layering etc), to 1–40 mm for tabletting technologies.

The IR and SR forms of the NMDA receptor antagonist are then combined into a single dosage such that the amount of NMDA receptor antagonist in the composition of the invention is in the range of about 1–5000 mg typically, 1 mg to 1000 mg, and preferably 100 mg to 800 mg. The composition including an NMDA receptor antagonist in an immediate release form in association with a NMDA receptor antagonist in a controlled release form may include an amount of NMDA receptor antagonist in the immediate release form of approximately 5% to 90% of the composition of the invention, preferably 10% to 60%. An immediate release NMDA receptor antagonist content of about 15% to 50% is particularly preferred. The controlled release form of the NMDA receptor antagonist may constitute the remainder of the active ingredient.

As a result, the final composition provides an amount of NMDA receptor antagonist for immediate release following administration and an additional amount of NMDA receptor antagonist for sustained release. The SR component is preferably aimed at reducing the dosage interval from 3 to 6 times daily to 1 or 2 times daily.

The composition of the invention may exhibit more than one peak in the plasma concentration/time curve in any one dosing interval depending on the particular NMDA receptor antagonist(s) used, the relative amounts of the IR and SR components, and the dissolution properties of the SR component.

The following non-limiting examples illustrate the uses of the components listed above in producing a composition in accordance with the invention.

Where the composition of the invention is in the form of a pellet product, the peltets may be presented in a sachet, capsule or tablet. The non limiting examples below describes pellet (particle sizes 200–1700 µm) in a capsule. All the quoted ranges are % w/w.

A plurality of elements containing the active ingredients (cores) are prepared by extrusion/marumerisation, or layering the active (or blend of active with other excipients) onto inert carriers by various processes. The cores themselves could be IR or SR depending on the materials and method of manufacture. The cores may contain the drug at the required potency according to the particular NMDA dose (mg), required size and presentation, and subsequent processes (coating etc.) The cores may contain drugs in the range 0.1–100% depending on the required dose, potency, manufacturing method, and properties.

An extruded core would typically include a carrier such as microcrystalline cellulose in the range 5–99.9%, a binder such as hydroxypropyl cellulose in the range 0–50%, a filler such as lactose in the range 0–50% and other excipients. An extruded core may only contain drug and binder.

An extruded core with SR properties would typically contain a swelling/gelling polymer such as hydroxypropyl cellulose in the range 0–50% or a hydrophobic material such as cetylalcohol in the range 10–90% with the drug. A layered core would contain an inert carrier such as a sugar sphere in the range 10–90% with a binder in the range 0.1–50% with the drug. The core may or may not contain fillers, solubilisers and other additives. The binder may be chosen to achieve IR (hydroxypropyl cellulose, hydroxypropyl methyl cellulose etc), or SR (ethyl cellulose, cellulose acetate butyrate etc), or delayed/modified release (ie enteric binding materials such as hydroxypropyl methyl cellulose phthalate, polyvinyl acetate phthalate etc).

A portion of the final dosage form may be IR cores made by the above described processes. Alternatively the IR cores may be coated with a rapidly disintegrating or dissolving coat for aesthetic, handling, or stability purposes. Suitable materials are polyvinylpyrrolidone, hydroxypropyl cellulose, hydroxypropyl methyl cellulose, polyethylene glycol, polymethacrylates containing free amino groups, each may be with or without plasticisers, and with or without an antitack agent or filler. An addition of about 3% of the weight of the core as coating material is generally regarded as providing a continuous coat for this size range.

The SR portion of the dose may be provided by a SR core as described above, a SR core which is further modified by overcoating, or an IR core which is modified by overcoating. The IR and SR NMDA receptor antagonist need not be the same active, nor are the IR or SR components of a dose themselves limited to just one active.

A typical coating composition for making the SR component would contain an insoluble matrix polymer in amounts approximately 15–85% by weight of the coating composition and a water soluble material in an amount of approximately 15–85% by weight of the coating composition. Optionally an enteric polymer in amounts from 0 to 100% by weight of the coating composition may be used or included. Suitable insoluble matrix polymers include ethyl cellulose, cellulose acetate butyrate, cellulose acetates, polymethacrylates containing quaternary ammonium groups or other pharmaceutically acceptable polymers. Suitable water soluble materials include polymers such as polyethylene glycol, hydroxypropyl cellulose, hydroxypropyl methyl cellulose, polyvinylpyrrolidone, polyvinyl alcohol, and monomeric materials such as sugars (eg lactose, sucrose, fructose, mannitol and the like), salts (eg. sodium chloride, potassium chloride and the like), organic acids (eg. fumaric acid, succinic acid, lactic acid, tartaric acid and the like) and mixtures thereof. Suitable enteric polymers include hydroxypropyl methyl cellulose, acetate succinate, hydroxypropyl methyl cellulose, phthalate, polyvinyl acetate phthalate, cellulose acetate phthalate, cellulose acetate trimellitate, shellac, zein, polymethacrylates containing carboxyl groups, and the like.

The coating composition may or may not be plasticised according to the properties of the coating blend such as the glass transition temperature of the main component or mixture of components or the solvent used for applying the coating compositions. Suitable plasticisers can be added from 0 to 50% by weight of the coating composition and at least one may be selected from diethyl phthalate, citrate esters, polyethylene glycol, glycerol, acetylated glycerides, acetylated citrate esters, dibutylsebacate, castor oil and the like.

The coating composition may or may not include a filler. The filler may comprise 0 to approximately 200% by weight based on the total weight of the coating composition and may be an insoluble material such as silicon dioxide, titanium dioxide, talc, kaolin, alumina, starch, powdered cellulose, MCC, polacrilin potassium, and the like.

The coating composition may be applied as a solution or latex in organic solvents or aqueous solvents or mixtures thereof. Where solutions are applied the solvent is present in amounts from approximate by 25–99% by weight preferably 85–97% by weight based on the total weight of dissolved solids. Suitable solvents are water, lower alcohol, lower chlorinated hydrocarbons, ketones or mixtures thereof.

Where latexes are applied, the solvent is present in amounts from approximately 25–97% by weight, preferably 60–97% based on the quantity of polymeric material in the latex. The solvent may be predominantly water.

A suitable tablet formulation may be of a swelling/gelling polymer such as L-hydroxypropyl cellulose admixed with a filler such as MCC and the drug. The tablet excipients may or may not be processed ie. spray dried together, prior to use in tabletting. The mixture may be compressed directly, or granulated prior to compression. Matrix tablets of this type often exhibit a rapid initial release until the polymers swell and gel, which induces SR for the remainder of the drug.

The quantity of IR and duration of SR can be varied by altering the quantities of the excipients used. If the IR component is not large enough, a quantity of drug can be included in a rapidly dissolving outer coat of polymers such as PEG or hydroxypropyl methyl cellulose. A typical matrix tablet would contain the swelling/gelling polymer in amounts from approximately 15 to 70% by weight based on the total weight of the tablet and filler in amounts from approximately 15 to 70% by weight based on the total weight of the tablet. Additional fillers may be included in amounts from approximately 0–60% by weight based on the total weight of the tablet. These may be soluble materials such as lactose, mannitol, sorbitol and the like, or insoluble materials such as tribasic calcium phosphate powdered cellulose or any of the various starches (corn, wheat, potato etc.) Additionally, the tablets may contain a lubricant in an amount from 0–8% by weight based on the total weight of the tablet. Lubricants may be selected from metal stearates, stearic acid, hydrogenated oils, such as soya bean oil or castor oil, sodium stearyl fumarate, polytetrafluoroethylene, talc and the like. The tablets may be coated for aesthetic, handling or stability purposes, or to increase the quantity of the IR portion of the drug. In this latter case the drug is dissolved or suspended in the coating solution and sprayed onto the tablets until the desired quantity of drug has been added. Suitable coating materials include polyethylene glycol, hydroxypropyl methyl cellulose, hydroxypropyl cellulose, polyvinyl alcohol, polyvinylpyrrolidone, sugar, waxes, or mixtures of these. The material may be added to any desired thickness but weight gains in the range 1–20% are typical, preferably 2–10%, more preferably 2–5%. The coat may or may not be plasticised. A plasticiser may be present in amounts from about 0–50% by weight based on the total weight of the tablet of the coating material. Examples of plasticisers are diethyl phthalate, citrate esters, acetylated citrate esters, polyethylene glycol, glycerol, dibutylsebacate, acetylated monoglycerides, castor oil and the like).

The coating composition may include an antitack agent such as talc, kaolin, titanium dioxide, silicon dioxide, alumina, starch, polacrilin potassium, microcrystalline cellulose or the like).

The coating materials may be applied to the drug particles, processed drug particles (ie. cores, granules), finished tablets, or finished capsules.

The coating composition may or may not include a filler. The filler may comprise 0 to approximately 200% by weight based on the total weight of the coating composition and may be an insoluble material such as silicon dioxide, titanium dioxide, talc, kaolin, alumina, starch, powdered cellulose, microcrystalline cellulose, polacrilin potassium.

The coat may contain other ingredients such as dyes and waxes.

The coat may be applied as a solution or suspension from aqueous or organic solvents solution concentration in equipment familiar to these skilled in the art. The coating composition may be applied as a solution or latex in organic solvents or aqueous solvents or mixtures thereof. Where solutions are applied the solvent is present in amounts from approximate by 25–99% by weight preferably 85–97% by weight based on the total weight of dissolved solids. Suitable solvents are water, lower alcohols, lower chlorinated hydrocarbons, keton es, or mixtures thereof. Where latexes are applied, the solvent is present in amounts from approximately 25–97% by weight, preferably 60–97% based on the quantity of polymeric material in the latex. The solvent may be predominantly water.

Alternatively the SR component of a tablet may be provided in the form of SR pellets and the IR component may be included in the body of the tablet. Such a tablet disintegrates to release the IR drug and the SR pellets. Pellets may be present in amounts from 1–60% by weight of the tablet, preferably 5–50% more preferably 5 40%. Suitable matrix materials for tablets of this type are microcrystalline cellulose, starches and the like.

The immediate release form of the NMDA receptor antagonist may be presented in a fast dissolving dosage form. The immediate release form may be in the form of a solid or molecular dispersion of the active within a polymer matrix. The polymer matrix may be selected from biologically acceptable polymer such as a cellulose ether, for example ethyl cellulose, or cellulose ester, for example cellulose acetate butyrate etc. The immediate release form may simply be particles of the antagonist or the antagonist deposited on a core containing the antagonist.

The composition of the invention, where it is in a tablet or like form, may include the two forms of the NMDA receptor antagonist as separate components, for example, in a multi-layer tablet, wherein one or more layer include the NMDA receptor antagonist in an immediate release form with one or more layers of the NMDA receptor antagonist in a controlled release form. Alternatively the composition of the invention may be in the form of a tablet wherein the immediate release forms the shell and the controlled release form constitutes the core.

Alternatively, the two forms of the NMDA receptor antagonist may be dispersed throughout the tablet.

The composition of the invention may be produced by providing a core containing the NMDA receptor antagonist controlled release component coated with an enteric or delayed release coating. The core can be in the form of beads compressed to a tablet. The coated core may then be compressed into tablets along with a powder mixture containing additional NMDA receptor antagonist or filled in combination with uncoated NMDA receptor antagonist into a capsule shell. As a result, the final composition provides an amount of NMDA receptor antagonist for immediate release following administration and an additional amount of NMDA receptor antagonist for controlled release.

The controlled release form of the NMDA receptor antagonist is such as to provide sustained release of the antagonist. Preferably the controlled or sustained release form provides a therapeutic effect over a period greater than about 6 hours. More preferably the sustained therapeutic effect is greater than about 8 hours. A sustained therapeutic effect period of 8 to 24 hours being especially preferred. The SR component of the controlled release composition is aimed at reducing the dosage interval from 3 to 6 times daily to 1 to 2 times daily.

The controlled release form of the antagonist may be coated beads or granules of the NMDA receptor antagonist. The coated antagonist may be combined with uncoated or lightly coated antagonist to provide a composition of the present invention. The term "lightly coated" as used in the description means a rapidly disintegrating coating for aesthetic, handling or stability purposes. These then may be filled into capsules or formed into tablets. Microencapsulation may also be used to produce the controlled release form of the NMDA receptor antagonist.

The coating or matrix material may be any suitable material. The coating or matrix material may be a polymer or a wax. The wax may be selected from any suitable wax or wax-like material including natural oil and fat and hardened oils such as hardened rapeseed oil, hardened castor oil, hardened beef tallow, palm oils and the like; waxes such as carnauba wax, bees wax, paraffin wax, ceresine wax, shellac wax or a fatty acid.

The present invention also provides a kit including a plurality of unit dosage forms, in a container or the like, the container including indicia indicative of a dosage regimen, at least one of the unit dosages being in the form of a pharmaceutical composition in accordance with the present invention.

The kit may further include unit dosages which provide immediate and controlled release of one or more actives such as an NMDA receptor antagonist. The kit may also include instructions for use of the kit.

Throughout the claims and description of this specification, the word "comprise" and variations of the word, such as comprising and "comprises", is not intended to exclude other additives, components, integers and steps.

The present invention will now be more fully described with reference to the accompanying example. It should be understood, however that the following description is illustrative only and should not be taken in any way as a restriction on the generality of the invention as specified above.

EXAMPLE 1

A DEXTROMETHORPHAN DISSOLUTION PROFILE

BACKGROUND

Figure 1:
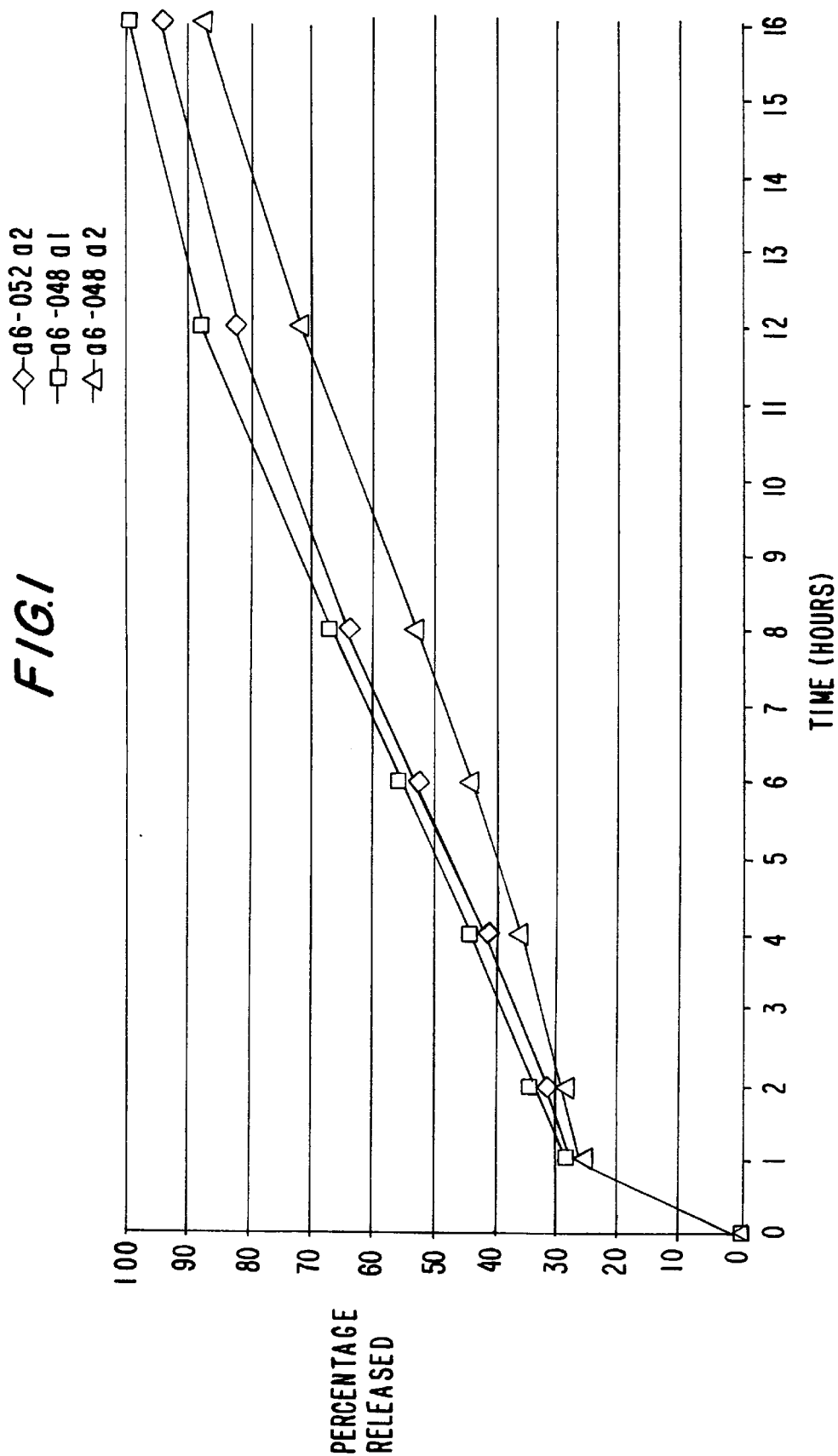
FIG. 1 shows the dissolution rate of sustain release dextromethorphan capsules.

Dextromethorphan (DM) is an NMDA receptor which has been in clinical use for many years. Pharmacokinetic data suggest that after a normal 60mg dose the absorption of the drug is quite rapid, reaching maximum plasma levels in 1 to 2 hours. However, the bioavailability of the drug is quite low, probably because of extensive first-pass hepatic metabolism. Once absorbed, DM is converted in the is body to a metabolite (dextrophan) which is reported to be pharmacologically active. Both the parent and the metabolite have short half-lives (2 to 4 hours).

Since DM and the active metabolite have short half-lives, a controlled release formulation will be useful to provide up to 24 hour delivery of this NMDA receptor antagonist from a single dose.

METHOD a) PRODUCTION OF DEXTROMETHORPHAN CAPSULES

Dextromethorphan capsules were prepared according to the following and dissolution profiles were determined on the capsules.

(i) Granulating Dextromethorphan Solution

| Ingredient | % (W/W) |
| --- | --- |
| Ethanol 96 PC/BP | 95.0 |
| Hydroxy Propyl Cellulose BP/NF | 5.0 |

Ethanol 96 PC/BP was added to a container. To this, Hydroxy Propyl Cellulose BP/NF was added while shear stirring. The solution was left to stir until all of the polymer was dissolved.

(ii) Coating Solutions

Formulation 1

| Ingredient | % (W/W) |
| --- | --- |
| Ethanol 96 PC/BP | 95.0 |
| Hydroxy Propyl Methyl Cellulose BP/USP 603 | 2.0 |
| Ethyl Cellulose N50 | 3.0 |

Ethanol 96 PC/BP and Hydroxy Propyl Methyl Cellulose BP/USP 603 were shear stirred. After the HPMC had dissolved, Ethyl Cellulose N50 was shear stirred into the solution. The solution was shear stirred until the Ethyl Cellulose had completely dissolved.

Formulation 2

| Ingredient | % (W/W) |
|---|---|
| Ethanol 96 PC/BP | 93.43 |
| Diethyl Phthalate BP/USP | 0.65 |
| Methacrylic Acid Copolymer NF, Type C Powder | 1.05 |
| Ethyl Cellulose N50 | 3.59 |
| Poly Ethylene Glycol (6000) NF | 1.28 |

The above ingredients were combined with stirring to produce Coating Formulation 2.

(iii) Dextromethorphan Cores

Dextromethorphan Cores Part 1

The cores containing dextromethorphan were produced in a fluid bed coater at the following conditions:

| Inlet Air Temperature: | 50° C. |
|---|---|
| Air Flow: | 80 m³/hr |

Two sets of dextromethorphan containing cores were produced; one with dextromethorphan potency of 57.75% and one with a potency of 80%. Both cores were made in a fluid bed coater with the ingredients listed below using standard methods known to those skilled in the art. The particle size range of the final cores was 710–1400 microns for the low potency cores and 1000–1700 microns for the high potency cores. In order that the desired capsule size would be used, the high potency cores were used in the next part of the process.

| Ingredient | % (W/W) | Typical Amounts (kg) |
|---|---|---|
| Ethanol 96 PC/BP | — | 0.200 |
| Dextromethorphan Granulating Solution | 43.82 | 1.560 |
| Dextromethorphan HBr | 33.71 | 1.200 |
| Sugar Spheres 30–35 Mesh | 22.47 | 0.800 |

Theoretical Potency at the end of Dextromethorphan Core Part 1 is 57.75%.

Dextromethorhan Core Part 2

The cores containing dextromethorphan were produced in a fluid bed coated at the following operating conditions:

| Inlet Air Temperature: | 50° C. |
|---|---|
| Air Flow: | 80 m³/hr |

| Ingredient | % (W/W) | Typical Amounts (kg) |
|---|---|---|
| Ethanol 96 PC/BP | — | 0.200 |
| Dextromethorphan Granulating Solution | 43.82 | 1.560 |
| Dextromethorphan HBr | 33.71 | 1.200 |
| Dextromethorphan Cores Part 1 | 22.47 | 0.800 |

Theoretical potency at the end of Dextromethorphan Core Part 2 is 80%.

The final core will have the following composition.

| Ingredient | % (W/W) |
|---|---|
| Dextromethorphan HBr | 79.98 |
| Hydroxy Propyl Cellulose BP/NF | 5.20 |
| Sugar Spheres (30–35) Mesh | 14.82 |

(iv) Dextromethorphan Pellets

The high potency dextromethorphan cores were dispensed with one of the coating formulations and talc in a fluid bed coater to produce the pellets. The process was run with the two different coating formulations and two different theoretical polymer coat weights (TPCW) were produced with Coating formulation 1. The conditions in the fluid bed coater are as follows:

| Inlet Air Temperature: | 50° C. |
|---|---|
| Air Flow: | 80 m³/hr |
| Dew Point: | 0° C. |

The pellets were produced by standard coating methods well known to those skilled in the art. The final pellets within the size range 1000–1700 microns were retained.

Aim Product for A6-048 A1 (8% Theoretical Polymer Coat Weight (TPCW)). A6-048 A1, A6-052 A2, and A6-048 A2 are batch numbers used to identify different pellet compositions.

| Ingredient | % (W/W) | Typical Amounts (kg) |
|---|---|---|
| Ethanol 96 PC/BP | — | 0.2000 |
| Coating Formulation 1 | 62.51 | 1.7400 |
| Talc Purified Micronised BP/USP | 1.56 | 0.0435 |
| Dextromethorphan Cores | 35.93 | 1.0000 |

Aim Product for A6-052 A2 (10% Theoretical Polymer Coat Weight (TPCVV)

| Ingredient | % (W/W) | Typical Amounts (kg) |
|---|---|---|
| Ethanol 96 PC/BP | — | 0.2000 |
| Coating Formulation 2 | 67.80 | 2.2222 |
| Talc Purified Micronised BP/USP | 1.69 | 0.0555 |
| Dextromethorphan Cores | 30.51 | 1.0000 |

The resulting Dextromethorphan Pellets have an excipient breakdown as follows.

Dextromethormhan Pellet A6-052 A2 (10% TPCW)

| Ingredient | % (W/W) |
|---|---|
| Dextromethorphan HBr | 68.56 |
| Hydroxy Propyl Cellulose BP/NF | 4.46 |
| Sugar Spheres (30–35) Mesh | 12.70 |
| Ethyl Cellulose N50 | 5.20 |
| Diethyl Phthalate BP/USP | 0.94 |
| Methacrylic Acid Copolymer NF, Type C Powder | 1.52 |

-continued

| Ingredient | % (W/W) |
|---|---|
| Poly Ethylene Glycol (6000) NF | 1.86 |
| Talc Purified Micronised BP/USP | 4.76 |

Dextro Pellet A6-048 A1 (8% TPCW)

| Ingredient | % (W/W) |
|---|---|
| Dextromethorphan HBr | 70.75 |
| Hydroxy Propyl Cellulose BP/NF | 4.60 |
| Sugar Spheres (30–35) Mesh | 13.11 |
| Hydroxy Propyl Methyl Cellulose BP/USP 603 | 3.08 |
| Ethyl Cellulose N50 | 4.61 |
| Talc Purified Micronised BP/USP | 3.85 |

Dextro Pellet A6-048-A2 has a 10% TPCW with the same extract coating solution.

(v) Capsules

Capsules were filled by blending cores with pellets. Each size 0, natural/natural capsule contained 250 mg of dextromethorphan. The ratio of core ADS equivalent to pellet ADS equivalent was 25/75. This meant that 62.5 mg of dextromethorphan was contained in the immediate release cores, and 187.5 mg of dextromethorphan was contained in the controlled release pellets. The potencies of each of the cores and pellets was determined by UV assay.

b) MEASUREMENT OF DISSOLUTION OF DEXTROMETHORPHAN CAPSULES

Dissolution was measured using USPXXIII apparatus and method for dissolution <711>, apparatus 1. The analysis measures the UV absorbance of dextromethorphan at 278 nm.

RESULTS

DISSOLUTION PROFILE OF DEXTROMETHORPHAN CAPSULES

Dissolution of the dextromethorphan capsules was measured according to the parameters above. The theoretical dissolution profile is compared with actual dissolution profile in Table 2 and shown in FIG. 1. An aim dissolution profile was established with reference to the pharmacokinetic parameters, derived from the literature of immediate release dextromethorphan.

TABLE 2

AIM AND ACTUAL DISSOLUTION

| | Aim | | | Actual | |
|---|---|---|---|---|---|
| Time (hours) | % Released | ± 20% limit | A6-048 A1 | A6-048 A2 | A6-052 A2 |
| 0.5 | 27.5 | 22–33 | 25.8 | 24.9 | 26.7 |
| 1 | 30 | 24–36 | 28.0 | 26.5 | 27.8 |
| 2 | 35 | 28–42 | 33.3 | 29.5 | 31.5 |
| 4 | 45 | 36–54 | 43.8 | 36.3 | 42.2 |
| 6 | 55 | 44–66 | 55.2 | 44.4 | 53.2 |
| 8 | 65 | 52–78 | 66.8 | 53.3 | 64.1 |
| 12 | 85 | 68–100 | 87.9 | 71.8 | 82.0 |
| 16 | 100 | >80 | 99.6 | 87.7 | 94.3 |

EXAMPLE 2

BACKGROUND

Amantadine is an NMDA receptor antagonist which has been in clinical use many years. Pharmacokinetic data for the drug are as follows: half life about 12 hours, bioavailability is high (assumed to be 100%), absorption rate constant is 0.693 per hr, and elimination rate constant 0.058 per hour. The normal dosage regimen is 200 mg per day given in two divided doses of 100 mg.

In designing a suitable once daily formulation, the primary aim is to ensure that the fluctuations in plasma concentrations (maximum divided by minimum) resulting from a dose of 200 mg once a day (sustained release) are equal to or less than those obtained with the use of immediate release formulation given twice daily. Simulations were performed using the above pharmacokinetic data to calculate a dissolution profile to achieve this minimum plasma concentration fluctuation. The product required had an immediate release component of 30% and a sustained release of the other 70% over approximately a 12 hour period at intestinal pH.

Method

Amantadine capsules were prepared according to the following and dissolution profiles were determined on the sustained release portion thereof.

| Amantadine fast release cores | |
|---|---|
| Amantadine hydrochloride | 2000 g |
| Microcrystalline cellulose | 2000 g |
| Purified water | 1680 g |

The materials were blended together and the resulting granulate was passed through a 1.2 mm screen using a Nica E 140 extruder. The extrudate was placed in portions on a Marumeriser (Q400, Fuji Paudal) until the desired roundness had been achieved. The product was dried in a Glatt WSG-3 fluid bed with an inlet air temperature of 50C. for 4 hours and then sieved between 1000 and 1700 um. The yield was 74.5%. The dissolution of these particles (USP XXIII, apparatus II) was rapid at both pH 1.2 and pH 6.8.

| Coating solution | |
|---|---|
| Ethyl cellulose N-50 | 200 g |
| Hydroxy propyl methyl cellulose E-5 | 22.5 g |
| Triethylcitrate | 27.5 g |
| Ethanol 96PC/BP | 4750 g |

Ethanol 96PC/BP and hydroxypropyl methyl cellulose E-5 were shear stirred. After the HPMC had dissolved ethyl cellulose N-50 was added and shear stirred until it had dissolved completely.

Amantadine Slow Release Pellets

The fast releasing cores were dispensed into a fluid bed coater. The conditions in the fluid bed coater were as follows:

| Inlet air temperature | 50° C. |
|---|---|
| Air flow | 80 meters cubed/hour |
| dew point | 0° C. |

The pellets were produced by coating methods standard to those skilled in the art.

The final pellets in the size range 1000–1700 um were retained.

| Coating formulation | 2720 g |
|---|---|
| Amantadine fast release cores | 1000 g |
| Talc USP | 68 g |

The talc was suspended in the coating solution and the suspension was sprayed onto the cores in the fluid bed coater. This resulted in a product with a theoretical polymer coat weight of 12%.

The resulting amantadine pellets have an excipient breakdown as follows:

| Amantadine hydrochloride | 41.53% |
|---|---|
| Microcrystalline cellulose | 41.53% |
| Talc | 5.64% |

-continued

| Ethyl cellulose | 9.04% |
|---|---|
| Hydroxy propyl methyl cellulose | 1.02% |
| Triethylcitrate | 1.24% |

Measurement of Dissoluition of Amantadine Sustained Release Pellets

Dissolution was measured using USPXXIII apparatus 1, method <711> with pH 6.8 dissolution media. Analysis was performed using the USPXXIII method for amantadine.

Figure 2:
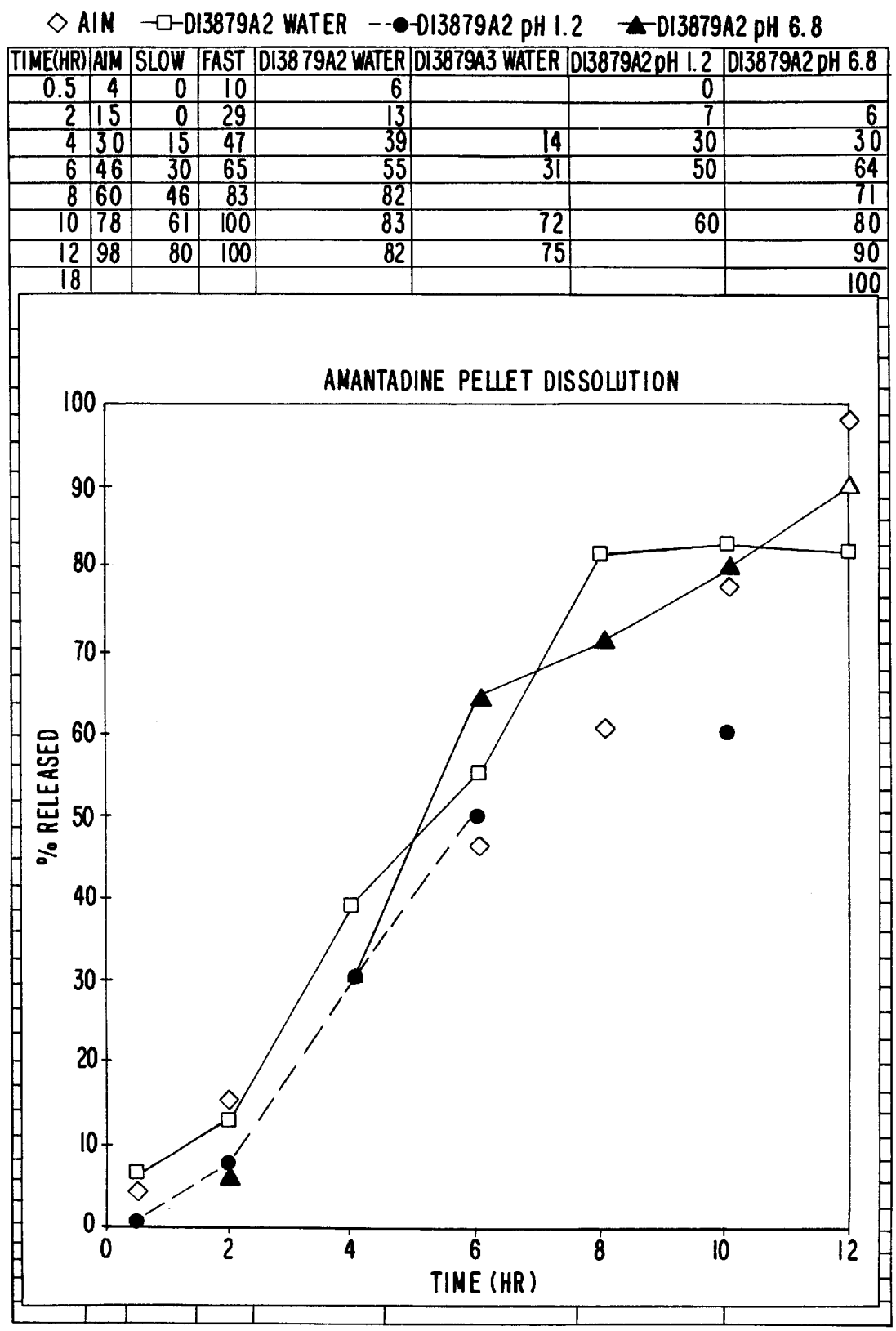
FIG. 2 shows the dissolution rate of amantadine pellets.

The dissolution profile of the sustained release portion was measured and compared with that calculated from the pharmacokinetic parameters. The results appear in Table 3 and are shown in FIG. 2.

TABLE 3

| Aim and actual dissolution | | |
|---|---|---|
| Time | % Released | Aim % Released |
| 2 | 4 | 17 |
| 4 | 30 | 33 |
| 6 | 64 | 50 |
| 8 | 70 | 67 |
| 10 | 80 | 83 |
| 12 | 90 | 100 |

The sustained release portion released 13% at 2 hours in pH 1.2 dissolution media, showing that the capsule does not dose dump in the stomach.

A combination of 30% of the dose as the starting core (120 mg of cores, equivalent to 60 mg of amantadine) and 70% of dose as the sustained release pellet (279 mg, equivalent to 140 mg of amantadine) will have dissolution properties substantially like the required profile of a once daily product. The dose combination fits into a size 0 capsule.

The terms and expressions which have been employed are used as terms of description and not of limitation, and there is no intention in use of such terms and expressions excluding any equivalents of the feature shown and described or portions thereof, it being recognized that various modifications are possible within the scope of the invention.

What is claimed is:

1. A method of preparing an analgesic pharmaceutical composition for the administration of an NMDA receptor antagonist to a human or animal subject for the treatment of pain, comprising:

providing a matrix or coated core containing an NMDA receptor antagonist to provide sustained release of a NMDA receptor antagonist;

providing a mixture containing a NMDA receptor antagonist to provide an immediate release of a NMDA receptor antagonist; and combining the matrix or coated core with the mixture, the immediate release form and sustained release form being present in sufficient amounts to diminish or abolish wind-up.

2. The method of claim 1 wherein the matrix core is a matrix composition selected from the group consisting of a wax; an insoluble matrix polymer; water soluble matrix materials and mixtures thereof.

3. The method of claims 1 wherein the coated core is a core of NMDA receptor antagonist coated with a pharmaceutically acceptable polymer including diffusion barrier polymers with or without porosity enhancers selected from the group consisting of ethyl cellulose, cellulose acetate butyrate, cellulose acetates, polymethacrylates containing quaternary ammonium groups, polyethylene glycol, hydroxypropyl cellulose, hydroxypropyl methyl cellulose, polyvinylpyrrolidone, polyvinyl alcohol, and monomeric materials, sugars, lactose, sucrose, fructose and mannitol, salts, sodium chloride, potassium chloride, organic acids, fumaric acid, succinic acid, lactic acid and tartaric acid and mixires thereof, enteric polymers, hydroxypropyl ceUlluose, hydroxypropyl methyl cellulose, polyvinyl acetate phthalate, cellulose acetate phthalate, cellulose acetate trimellitate, shellac, zein, and polymethacrylates containing carboxyl groups.

4. The method of claim 1 further comprising compressing the core and the mixture into a tablet form and wherein the core and the mixture are dispersed throughout the tablet form.

5. The method of claim 1 wherein the core and the mixture are combined and compressed into a tablet form such that the core and the mixture form a multilayer tablet form.

6. The method of claim 1 wherein the core and the mixture are combined into a capsule.

7. A method for the therapeutic or prophylactic treatment of pain related to wind-up in a human or animal subject, the method comprising administering to the subject an effective amount of an analgesic pharmaceutical composition including an NMDA receptor antagonist in an immediate release form combined with an NMDA receptor antagonist in a sustained release form, the immediate release form and sustained release form being present in sufficient amounts to diminish or abolish wind-up.

8. The method of claim 7 wherein the analgesic pharmaceutical composition is in an unit dosage form.

9. The method of claim 7 for the treatment of chronic or acute pain.

10. The method of claim 9 wherein the analgesic pharmaceutical composition is administered pre-operatively.

11. The method of claim 7 wherein the pain is related to hyperalgesia or alkodynia.

12. A method for the treatment of Huntington's disease amyotrophic lateral sclerosis (ALS), AIDS-related dementia, Alzheimer's disease, schizophrenia, motoneurone diseases and CNS and brain injuries resulting from a number of causes including trauma, stroke and neurosurgery in a human or animal subject, the method comprising administering to the subject an effective amount of an analgesic pharmaceutical composition including an NMDA receptor antagonist in an immediate release form combined with an NMDA receptor antagonist in a sustained release form, the immediate release form and sustained release form being present in sufficient amounts to diminish or abolish wind-up.

13. The method of claim 7 wherein the NMDA receptor antagonist is present in an amount of from about 1 to 5000 mg.

14. The method of claim 7 wherein the NMDA receptor antagonist is present in an amount of from about 1 to 1000 mg.

15. The method of claim 7 wherein the NMDA receptor antagonist is present in an amount of from about 100 to 800 mg.

16. The method of claim 12 wherein the NMDA receptor antagonist in the immediate release form comprises 5% to 90% of the total amount of the NMDA receptor antagonist.

17. The method of claim 16 wherein the NMDA receptor antagonist in the immediate release form comprises 10%–60% of the total amount of the NMDA receptor antagonist.

18. The method of claim 17 wherein the NMDA receptor antagonist in the immediate release form comprises 15%–50% of the total amount of the NMDA receptor antagonist.

19. The method of claim 7 wherein the NMDA receptor antagonist in an immediate release form is combined in a singe dosage form with an NMDA receptor antagonist in a sustained released form.

20. The method of claim 19 wherein a portion of the NMDA receptor antagonist is immediately released following administration and a portion is sustained released to provide a therapeutic effect over a period of greater than 6 hours.

21. The method of claim 20 wherein the therapeutic effect is provided over a period of 8 to 24 hours.

22. The method of claim 21 wherein the therapeutic effect is provided over a period of 8 to 12 hours.

23. The method of claim 21 wherein the therapeutic effect is provided over a period of 12 to 24 hours.

24. The method of claim 7 wherein the NMDA receptor antagonist in the immediate release or sustained release form is the same or different.

25. The method of claim 7 wherein the immediate release or sustained release form are in a form selected from the group consisting of active cores comprising; tablets; multilayered tablets; capsules containing coated active cores and/or uncoated active cores; liquids; powder; coated or uncoated granules; coated or uncoated pellets; suspensions; an injectable solution; a suppository; implant; transdermal patch; and osmotic pump.

26. The method of claim 25 wherein the immediate release and sustained release form of the NMDA receptor antagonist are separate components in a multi-layer tablet and one or more layers include the NMDA receptor antagonist in an immediate release form and one or more layers include the NMDA receptor antagonist in a sustained release form.

27. The method of claim 26 wherein the immediate release and sustained release forms of the NMDA receptor antagonist are dispersed throughout the tablet.

28. The method of claim 25 wherein the immediate release and sustained release form of the NMDA receptor antagonist are separate components in a capsule and one or more components include the NMDA receptor antagonist in an immediate release form and one or more components include the NMDA receptor antagonist in a sustained release form.

29. The method of claim 28 wherein one or more of the components are active cores or pellets and wherein the active cores are uncoated or coated for immediate or sustained release and wherein the pellets are coated for sustained release.

30. The method of claim 29 comprising a blend of cores and pellets wherein a ratio of cores to pellets is 25/75.

31. The method of claim 7 wherein the NMDA receptor antagonist is a morphinan selected from the group consisting of dextromethorphan and dextrorphan, ketamine, amantadine, memantine, eliprodil, ifenprodil, dizocilipine, remacemide, lamotrigine, riluzole, aptiganel, phencyclidine, flupirtine, celfotel, felbamate, spermine, spermidine, levemopamil, a pharmaceutically acceptable salt or ester thereof or a metabolic precursor of any of the foregoing.

32. The method of claim 7 wherein the sustained release form of the NMDA receptor antagonist is in a matrix composition selected from the group consisting of waxes; insoluble matrix polymer; and water soluble matrix material and mixtures thereof.

33. The method of claim 32 wherein the sustained release form farther includes an enteric polymer selected from the group consisting of hydroxypropyl cellulose, hydroxypropyl methyl cellulose, polyvinyl acetate phthalate, cellulose acetate phthalate, cellulose acetate trirellitate, shellac, zein, polymethacrylates containing carboxyl groups and combinations thereof.

34. The method of claim 33 wherein the composition further includes a binder selected from the group consisting of hydroxypropyl cellulose, hydroxypropyl methyl cellulose, ethyl cellulose, cellulose acetate butyrate, or an enteric binding material, hydroxypropyl methyl cellulose phthalate, polyvinyl acetate phthalate or mixtures thereof.

35. The method of claim 7 wherein the immediate release or sustained release form is coated with a pharmaceutically acceptable coating composition selected from the group consisting of ethyl cellulose, cellulose acetate butyrate, cellulose acetates, polymethacrylates containing quaternary ammonium groups, pharmaceutically acceptable polymers, polyethylene glycol, hydroxypropyl cellulose, hydroxypropyl methyl cellulose, polyvinylpyrrolidone, polyvinyl alcohol, and monomeric materials, sugars, lactose, sucrose, fructose and mannitol, salts, sodium chloride, potassium chloride and derivatives, organic acids fumaric acid, succinic acid, lactic acid and tartaric acid and mixtures thereof and enteric polymers, hydroxypropyl cellulose, hydroxypropyl methyl cellulose, polyvinyl acetate phthalate, cellulose acetate phthalate, cellulose acetate trimellitate, shellac, zein, and polymethacrylates containing carboxyl groups.

36. The method of claim 35 wherein the coating composition comprises from 0 to 50% by weight of a material selected from the group consisting of silicon dioxide, titanium dioxide, talc, kaolin, alumina, starch, powdered cellulose, MCC, polacrilin potassium, or mixtures thereof.

37. The method of claim 36 wherein the composition further comprises 0 to 200 wt. –% of a filler selected from the group consisting of silicon dioxide, titanium dioxide, talc, kaolin, alumina, starch, powdered cellulose, microcrystalline cellulose, polacrilin potassium, or mixtures thereof.

38. The method of claim 37 wherein the composition fer comprises a swelling/gelling polymer selected from the group consisting of hydroxypropyl cellulose in the range of 0–50 wt. –% or a hydrophobic material, in the range 10–90 wt. –%.

39. The method of claim 7 wherein the analgesic pharmaceutical composition is in a form suitable for oral or rectal administration or for administration by transdermal, intravenous, intramuscular, subcutaneous, intrathecal, epidural or intracerebroventricular means.

40. The method of claim 38 wherein the swelling/gelling polymer is cetyl alcohol.

41. The method of claim 35 wherein the enteric polymer is selected from the group consisting of hydroxypropyl cellulose, hydroxypropyl methyl cellulose, polyvinyl acetate phthalate, cellulose acetate phihalate, cellulose acetate trimellitate, shellac, zein, polymethacrylates containing carboxyl groups and mixtures thereof.

42. The method of claim 2 wherein the wax is selected from the group consisting of carnauba, bees wax, paraffin wax, ceresine, shellac, fatty acids, fatty alcohols; oils, hardened oils or fats, hardened rapeseed oil, castor oil, beef tallow, palm oil and soya bean oil; the insoluble matrix polymer is selected from the group consisting of ethyl cellulose, celulose acetate butyrate, cellulose acetates, polymethacrylates cotaining quaternary ammonium groups; and the water soluble matrix material is selected from the group consisting of polyethylene glycol, hydroxypropyl cellulose, hydroxypropyl methyl cellulose, polyvinylpyrrolidone, polyvinyl alcohol, and monomeric materials selected from the group consisting of sugars, salts, and organic acids.

43. The method of claim 7 wherein the immediate release form of the NMDA receptor antagonist is particles admixed with at least one component selected from the group consisting of cellulose, hydroxypropyl methyl cellulose; a surfactant selected from the group consisting of sodium lauryl sulphate, chremophor, tweens, spans, pluronics; an insoluble component selected from the goup consisting of microcrystalline cellulose, $Ca_3(PO_4)_2$, talc, fumed silica; a coating material selected from the group consisting of polyethylene glycol, hydroxypropyl methyl cellulose, wax, fatty acids and combinations thereof.

44. A method for the therapeutic or prophylactic treatment of pain related to wind-up in a human or animal subject, the method comprising administering to the subject an effective amount of an analgesic pharmaceutical composition including an NMDA receptor antagonist in an immediate release form combined with an NMDA receptor antagonist in a sustained release form, the immediate release form and sustained release form being present in sufficient amounts to diminish or abolish wind-up wherein the analgesic pharmaceutical composition comprises dextromorphan or a salt thereof in a dosage form wherein the dissolution rate in vitro of the dosage form, when measured by the USP Paddle Method at 100 rpm at 900 ml aqueous buffer at a pH of between 1.6 and 7.2 at 37° C. is between 22 and 33 wt. –% dextromorphan released after 0.5 hr, between 24 and 36 wt. –% dextromethorphan released after 1 hour, between 28 and 42 wt. –% dextromethorphan released after 2 hours, between 36 and 54 wt. –% dextromethorphan released after 4 hours, between 44 and 66 wt. –% dextromethorphan released after 6 hours, between 52 and 78 wt. –% dextromethorphan released after 8 hours, between 68 and 100 wt. –% dextromethorphan released after 12 hours, and greater than 80 wt. –% dextromethorphan released after 16 hours.

45. The method of claim 32 wherein the wax is selected from the group consisting of carnauba, bees wax, paraffin wax, ceresine, shellac, fatty acids, fatty alcohols, oils, hardened oils or fats, rapeseed oil, castor oil, beef tallow, palm oil, soya bean oil; the insoluble matrix polymer is selected from the group consisting of ethyl cellulose, cellulose acetate butyrate, cellulose acetates, polymethacrylates containing quaternary ammonium groups, pharmaceutically acceptable polymers; and the water soluble matrix material is selected from the group consisting of, polyethylene glycol, hydroxypropyl cellulose, hydroxypropyl methyl cellulose, polyvinylpyrrolidone, polyvinyl alcohol, monomeric materials, sugars, lactose, sucrose, fructose, mannitol, salts, sodium chloride, potassium chloride, organic acids, fumaric acid, succinic acid, lactic acid, tartaric acid and mixtures thereof.

46. The method of claim 7 wherein the intermediate release form of the NMDA receptor is a dispersion in a suitable material selected from the group consisting of wax; polymers; hardened oils or fats including, hardened rapeseed oil, hardened castor oil, hardened beef tallow, palm oils and soya bean oil; a soluble agent and combinations thereof.

47. The method of claim 42 wherein the sugar is selected from the group consisting of lactose, sucrose, fructose and mannitol; the salt is selected from the group consisting of sodium chloride and potassium chloride, and the organic acid is selected from the group consisting of fumaric acid, succinic acid, lactic acid and tartaric acid.

48. The method of claim 46 wherein the soluble agent is selected from the group consisting of lactose, mannitol, sorbitol and combinations thereof.

* * * * *